(12) United States Patent
Ikegami et al.

(10) Patent No.: US 8,274,048 B2
(45) Date of Patent: Sep. 25, 2012

(54) SCANNING ELECTRON MICROSCOPE HAVING TIME CONSTANT MEASUREMENT CAPABILITY

(75) Inventors: Akira Ikegami, Hitachinaka (JP);
Hideyuki Kazumi, Hitachinaka (JP);
Koichiro Takeuchi, Hitachinaka (JP);
Atsushi Kobaru, Hitachinaka (JP);
Seiko Oomori, Kokubunji (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 12/823,296

(22) Filed: Jun. 25, 2010

(65) Prior Publication Data

US 2010/0258723 A1    Oct. 14, 2010

Related U.S. Application Data

(63) Continuation of application No. 11/936,377, filed on Nov. 7, 2007, now Pat. No. 7,763,852.

(30) Foreign Application Priority Data

Nov. 8, 2006 (JP) ................. 2006-303067

(51) Int. Cl.
*G01N 23/00* (2006.01)
(52) U.S. Cl. ......... 250/311; 250/306; 250/307; 250/310

(58) Field of Classification Search .................. 250/306, 250/307, 310, 311
See application file for complete search history.

(56) References Cited

U.S. PATENT DOCUMENTS

| 5,302,828 | A | 4/1994 | Monahan |
| 5,412,209 | A | 5/1995 | Otaka et al. |
| 6,211,518 | B1 | 4/2001 | Richardson et al. |
| 2005/0045820 | A1 * | 3/2005 | Ohshima et al. ............... 250/310 |

FOREIGN PATENT DOCUMENTS

| JP | 62-052841 | 3/1987 |
| JP | 5-151927 | 6/1993 |
| JP | 07-014537 | 1/1995 |
| JP | 2001-508592 A | 6/2001 |
| JP | 3238705 P | 10/2001 |

* cited by examiner

Primary Examiner — Michael Maskell
(74) Attorney, Agent, or Firm — Crowell & Moring LLP

(57) ABSTRACT

In a scanning electron microscope, an optimum scanning method for reducing the amount of deflection of a primary electron beam and secondary electrons is determined to acquire stable images. An energy filter is used to discriminate between energy levels. The change in yield of obtained electrons is used to measure the variation in specimen potential. The time constant of charging created during electron beam irradiation is extracted. The scanning method is optimized based on the extracted time constant to reduce the distortion and magnification variation that appear in a SEM image.

5 Claims, 6 Drawing Sheets

D1: TEMPORAL CHANGE IN THE NUMBER OF DETECTED ELECTRONS
D2: SCANNING CONDITIONS

D1: TEMPORAL CHANGE IN THE NUMBER OF DETECTED ELECTRONS
D2: SCANNING CONDITIONS (a) ARRANGEMENT OF SCAN POINTS FOR TV SCANNING (b) WHEN TIME AND DISTANCE HAS EQUAL INFLUENCE (c) WHEN TIME CONSTANT IS LARGE (d) WHEN TIME CONSTANT IS SMALL

SCANNING ELECTRON MICROSCOPE HAVING TIME CONSTANT MEASUREMENT CAPABILITY

CROSS REFERENCE TO RELATED APPLICATION

This application is a continuing application of U.S. application Ser. No. 11/936,377, filed Nov. 7, 2007, which claims priority under 35 U.S.C. §119 to Japanese Patent Application No. 2006-303067, filed Nov. 8, 2006, the entire disclosure of which are herein expressly incorporated by reference.

BACKGROUND OF THE INVENTION

1. Field of the Invention

The present invention relates to an electron microscope that uses an electron beam to observe a specimen, and for example to a scanning electron microscope that detects electrons emitted from a specimen under electron beam irradiation to measure or examine the shape and composition of the specimen.

2. Background Art

Miniaturization and large-scale integration of ULSI (Ultra-Large Scale Integration) elements have been accelerated, so that devices are now processed at dimensions of several tens of nanometers. Furthermore, there have been increasingly developed multilayered devices using various types of new materials, such as low dielectric constant films and metal gate films to achieve higher speeds, as well as three-layer resist films to enhance etching resistance. To this end, tighter critical dimension (CD) management during ULSI processing has been required.

In semiconductor processing steps, insulators, such as resist films, insulating films, and low-k materials, are frequently used. When the surface of such an insulator (specimen) is irradiated with an electron beam, the surface is charged. The charged specimen not only changes the amount of secondary electrons that attempt to escape from the surface of the specimen but also bends the trajectory of the primary electron beam, resulting in distortion of images obtained by a scanning electron microscope. As a result, it is difficult to measure true dimensions and shapes after processing. For example, in the case of an ArF resist, it cannot be judged whether line edge roughness (LER) has occurred in an etching step or charging in the electron microscope has caused an error in dimension measurement. There are also problems in observation of contact hole having a large aspect ratio, such as distortion of the observed shape of the contact hole, and difficulty in identifying whether the observed hole diameter is either the upper or lower diameter. The charged state not only spatially changes due to the motion and diffusion of the electrons but also spatially and temporally changes due to, for example, hole-electron recombination-related attenuation. Furthermore, the specimen may be "positively charged" or "negatively charged" depending on observation conditions (the energy of the electron incident on the surface of the specimen, the magnification, the amount of electric current, and the scanning method). It is therefore important to control the charged state.

Conventional methods for controlling the charged state are summarized as follow: For example, JP Patent Publication (Kokai) No. 5-151927 (1993) (corresponding to U.S. Pat. No. 5,412,209) describes a method for stably acquiring images by performing primary electron irradiation at a low magnification different from that for observation (pre-dose) to intentionally charge an area larger than the observation area so as to obtain a uniformly charged observation area. In JP Patent Publication (Kokai) No. 7-14537 (1995), positive or negative charging is cancelled or reduced to alleviate the influence of the charging on observation by in advance performing an electron beam irradiation having energy different from that of the primary electron beam for observation. In JP Patent Publication (Kohyo) No. 2001-508592 (corresponding to U.S. Pat. No. 6,211,518), which discloses a similar technology, the observation area and a larger surrounding area are flooded (irradiated) with positive electric charge during a plurality of frame cycles to reduce the voltage difference between the scanned area and the surrounding area, and then the observation area is separately scanned to obtain a bright image of the observation area. JP Patent No. 3238705 (corresponding to U.S. Pat. No. 5,302,828) discloses a scanning technology by which the influence of surface electric charge is reduced when a substantially circular hole is scanned. There is another method in which the center position of a hole is identified in a low magnification, and the electron beam scan is repeatedly carried out from the center of the hole to a point beyond the edge of the hole in the outward radial direction in a high magnification. These technologies are designed to reduce the influence of charging and stably acquire accurate images.

JP Patent Publication (Kokai) No. 62-52841 (1987) discloses a method for measuring charging potential including the steps of determining the time constant of brightness from change in brightness of each of a plurality of images and outputting these time constants as potential information.

SUMMARY OF THE INVENTION

It is known that, in general, the amount and distribution of charging on the surface of an insulator specimen greatly depends on the following factors:

a) Changes depending on the energy of primary electrons, current density, observation magnification, and yield of secondary electrons/backscattered electrons from the specimen b) Temporal changes depending on the motion and diffusion of electrons, loss of electrons due to electron-hole recombination and the like c) Changes depending on the scanning method JP Patent Publication (Kokai) No. 5-151927 (1993) (corresponding to U.S. Pat. No. 5,412,209) is, as described above, a method for stabilizing images by charging an area larger than the observation area through pre-dosing to make the potential in the observation area substantially uniform. In this case, although the influence of charging is made substantially uniform, temporal changes in charged state described in b) and the fact that the charged state deflects the trajectories of electrons during the next scan described in c) are not considered. Images may therefore be changed or distorted in a disadvantageous manner depending on the scan interval and the number of scans.

In JP Patent Publication (Kokai) No. 7-14537 (1995), positive or negative charging is reduced by performing in advance an electron beam irradiation having energy different from that of the primary electron beam for observation. In this case, for example, when the specimen is positively charged in the preliminary irradiation and then irradiated with electrons having a negatively charging energy level during observation, the amount of charging in the observation area is reduced. However, the amount and distribution of charging change with time, and the distribution of charging in the scanned area differs from that in the non-scanned area. That is, since the phenomena described in b) and c) are not considered, there is no guarantee that the resultant scanned image is a "true" image, and the resultant image changes depending on the scan time and the number of scans. JP Patent Publication (Kohyo) No. 2001-508592 (corresponding to U.S. Pat. No. 6,211,518) has similar problems.

In the method disclosed in JP Patent No. 3238705 (corresponding to U.S. Pat. No. 5,302,828) in which the electron beam scan is carried out from the center of a circular hole toward the outside, electric charge is accumulated at the bottom of the hole, so that the electron beam irradiation to the center in the next scan is disadvantageously deflected. The deflection changes depending on the time required for the scan and the number of scans, so that it is difficult to stably acquire a true image.

In the method disclosed in JP Patent Publication (Kokai) No. 62-52841 (1987) in which changes in brightness in a plurality of images are used to display the potential distribution, the changes in brightness primarily result from the fact that the influence of charging causes low-energy emitted electrons to return to the specimen and that the trajectories of the low-energy emitted electrons are deflected so that the electrons cannot be not detected. From these reasons, the outputted potential information greatly depends on the energy distribution of the emitted electrons and the size of the charged area. It is therefore difficult to measure the accurate change in charging potential.

The present invention has been made in view of such circumstances and aims to provide a scanning electron microscope capable of acquiring stable images by determining an optimized scanning method in which the amounts of deflection of the primary electron beam and secondary electrons are reduced.

To solve the above problem, the present invention provides a method for measuring the charged state of a specimen and using the measurement result to determine the electron beam scanning order in which the influence of charging is reduced.

In general, the yield of secondary electrons/backscattered electrons varies depending on the energy for accelerating electrons for each material used in a ULSI device, and the distribution and potential of charging vary depending on the current density of the electron beam and the observation magnification. It is therefore necessary to monitor the charging that varies with time for each material. In the present invention, an energy filter is used to discriminate among energy levels of emitted electrons, and the behavior of electrons having a specific energy level (in particular, high-energy electrons emitted from the specimen) is investigated.

That is, the present invention provides a scanning electron microscope in which a specimen is irradiated with a primary electron beam to acquire an image of the specimen. The scanning electron microscope comprises an energy filter for catching electrons having at least a predetermined energy level among the electrons emitted from the specimen, time constant extraction means for extracting the time constant of a temporal change curve indicative of the relationship of the signal magnitude of the electrons caught by the energy filter with the electron beam irradiation time, and scanning order determination means for determining the scanning order in which the electron beam scans the specimen based on the extracted time constant. The specimen is scanned and observed in the determined scanning order.

The scanning order determination means may determine the scanning order based on the extracted time constant and scanning conditions defined by the one-line scan time and the scan interval in such a way that scan points are arranged in a time-distance space and the distance between each pair of the scan points is maximized. The scanning order is also determined in such a way that the scan points are arranged in a triangular, rectangular or hexagonal manner. The scanning order determination means may change the aspect ratio of the scan points arranged in the time-distance space according to the result of comparison of the time constant of the potential variation resulting from the electron beam irradiation to a reference time constant.

The time constant extraction means sets the filter potential of the energy filter to a fixed value and extracts the time constant of the potential variation from the temporal change in brightness produced when the specimen is irradiated with the primary electron beam. The time constant extraction means controls electron beam irradiation means in such a way that the specimen is irradiated with the primary electron beam at a plurality of positions on the specimen by shifting the irradiation position of the primary electron beam, and provides the temporal change curve by averaging the temporal changes in brightness obtained at the plurality of positions to extract the time constant of the potential variation.

The method for determining the scanning order according to the present invention is a method for determining the order in which a specimen is scanned in a scanning electron microscope in which the specimen is irradiated with a primary electron beam to acquire an image of the specimen. The method comprises the time constant extraction step of extracting the time constant of a temporal change curve indicative of the relationship of the signal magnitude of the electrons caught by an energy filter for catching electrons having at least a predetermined energy level among the electrons emitted from the specimen with the electron beam irradiation time, and the scanning order determination step of determining the scanning order in which the electron beam scans the specimen based on the extracted time constant.

The present invention also provides a scanning electron microscope in which a specimen is irradiated with a primary electron beam to acquire an image of the specimen.

The scanning electron microscope comprises an energy filter for catching electrons having at least a predetermined energy level among the electrons emitted from the specimen, time constant recording means for recording the time constant of a temporal change curve indicative of the relationship of the signal magnitude of the electrons caught by the energy filter with the electron beam irradiation time for each specimen to be observed in advance, specimen specifying means for specifying a specimen to be observed according to an instruction input, and scanning order determination means for acquiring the time constant corresponding to the specified specimen from the time constant recording means and determining the scanning order in which the electron beam scans the specimen to be observed based on the time constant. The specimen is scanned and observed in the determined scanning order.

The present invention also provides a scanning electron microscope in which a specimen is irradiated with a primary electron beam to acquire an image of the specimen. The scanning electron microscope comprises scanning order storing means for recording the scanning order in which the electron beam scans the specimen for each specimen to be observed in advance, specimen specifying means for specifying a specimen to be observed according to an instruction input, and scanning means for acquiring the scanning order corresponding to the specified specimen from the scanning order storing means and scanning the specimen with the primary electron beam based on the scanning order. For each specimen, the time constant of a temporal change curve indicative of the relationship of the signal magnitude of the electrons caught by an energy filter for catching electrons having at least a predetermined energy level among the electrons emitted from the specimen with the electron beam irradiation time is extracted, and the scanning order is determined based on the extracted time constant.

Additional features of the present invention will be apparent from the following best mode for carrying out the present invention and the accompanying drawings.

According to the present invention, an optimum scanning order (most resistant to the influence of charging produced by electron beam irradiation) can be determined, and accurate, stable images can be acquired by scanning a specimen in the scanning order.

DETAILED DESCRIPTION OF THE PREFERRED EMBODIMENTS

An embodiment according to the present invention will be described below in detail with reference to the accompanying drawings. The embodiment according to the present invention is only an example to implement the present invention, and the present invention is not limited thereto.
<Device Configuration>

Figure 1:
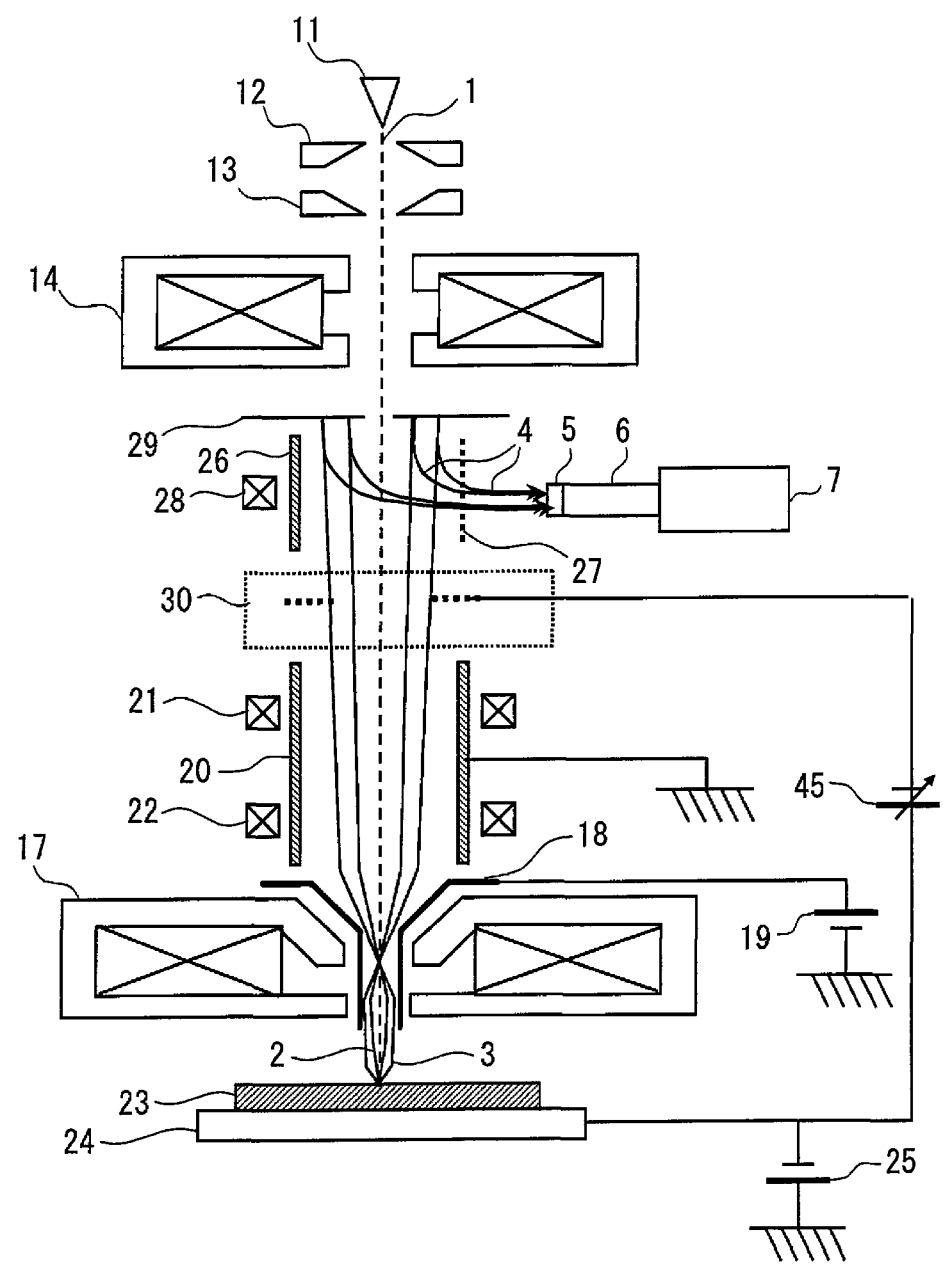
FIG. 1 shows a whole schematic configuration of the SEM of the present invention.

FIG. 1 shows a schematic configuration of a SEM (Scanning Electron Microscope) used in the embodiment of the present invention. An extracting voltage 13 is applied between a field emission electrode 11 and an extracting electrode 12 to generate a primary electron beam 1. The primary electron beam 1 undergoes scanning deflection through a condenser lens 14, an upper scanning deflector 21, and a lower scanning deflector 22. The magnitude of deflection produced in the upper scanning deflector 21 and the lower scanning deflector 22 is adjusted in such a way that a specimen 23 is scanned in a two dimensional manner using the center of an objective lens 17 as a pivotal point. The deflected primary electron beam 1 is further accelerated by a rear-stage acceleration voltage 19 in an acceleration cylinder 18 provided in the passage in the objective lens 17. The primary electron beam 1 that has undergone the rear-stage acceleration is focused by the lens effect of the objective lens 17 into a fine spot on the specimen 23.

When the specimen 23 is irradiated with the primary electron beam 1, secondary signals 2 and 3 are generated. The secondary signals under consideration are low-energy secondary electrons 2 and high-energy secondary electrons 3. The electric field created between the objective lens 17 and the specimen 23 acts on the generated secondary signals as an acceleration electric field, so that the secondary signals are attracted into the passage in the objective lens 17 and go upward under the lens effect of the magnetic field in the objective lens 17. The secondary signals 2 and 3 that have passed through the objective lens 17 then pass through the scanning deflectors 22 and 21, and enter an energy filter 30. The low-energy secondary electrons 2 cannot pass through the energy filter 30, while the high-energy secondary electrons 3 pass through the energy filter 30. When the specimen 23 keeps being irradiated with the primary electron beam 1, the specimen 23 is charged and specimen potential Vs changes. It is noted that the specimen potential Vs is the sum of the charging potential $\Delta Vs$ created by the electron beam irradiation and retarding potential 25 applied to a specimen holder 24. When the charging increases the specimen potential Vs ($=Vr+\Delta Vs$), the number of secondary electrons that can pass through the energy filter 30 decreases, so that signal electrons 4 detected at a detector 7 decreases.

Figure 2:
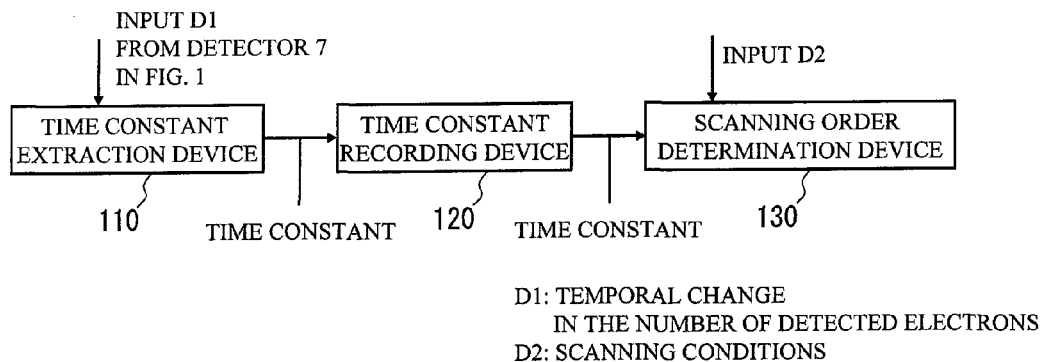
FIG. 2 is a device configuration diagram showing the flow from extraction of the time constant to determination of the scanning order according to an embodiment of the present invention.

As shown in FIG. 2, which is a configuration diagram showing the flow from extraction of the time constant to determination of the scanning order, the output of the detector 7 is supplied to a time constant extraction device 110 as an input D1. The time constant extraction device 110 extracts two time constants of the charging $\tau_1$ and $\tau_2$ from the input data D1 (see FIG. 7). The extracted time constant $\tau_1$ and $\tau_2$ is stored in a time constant recording device 120, and the stored time constant and scanning conditions D2 (scan interval $\Delta 1$ and the number of scans n) are used to determine the scanning order in a scanning order determination device 130. Then, the electron beam scans the specimen according to the determined scanning order to observe the specimen.
<Process Sequence>

Figure 3:
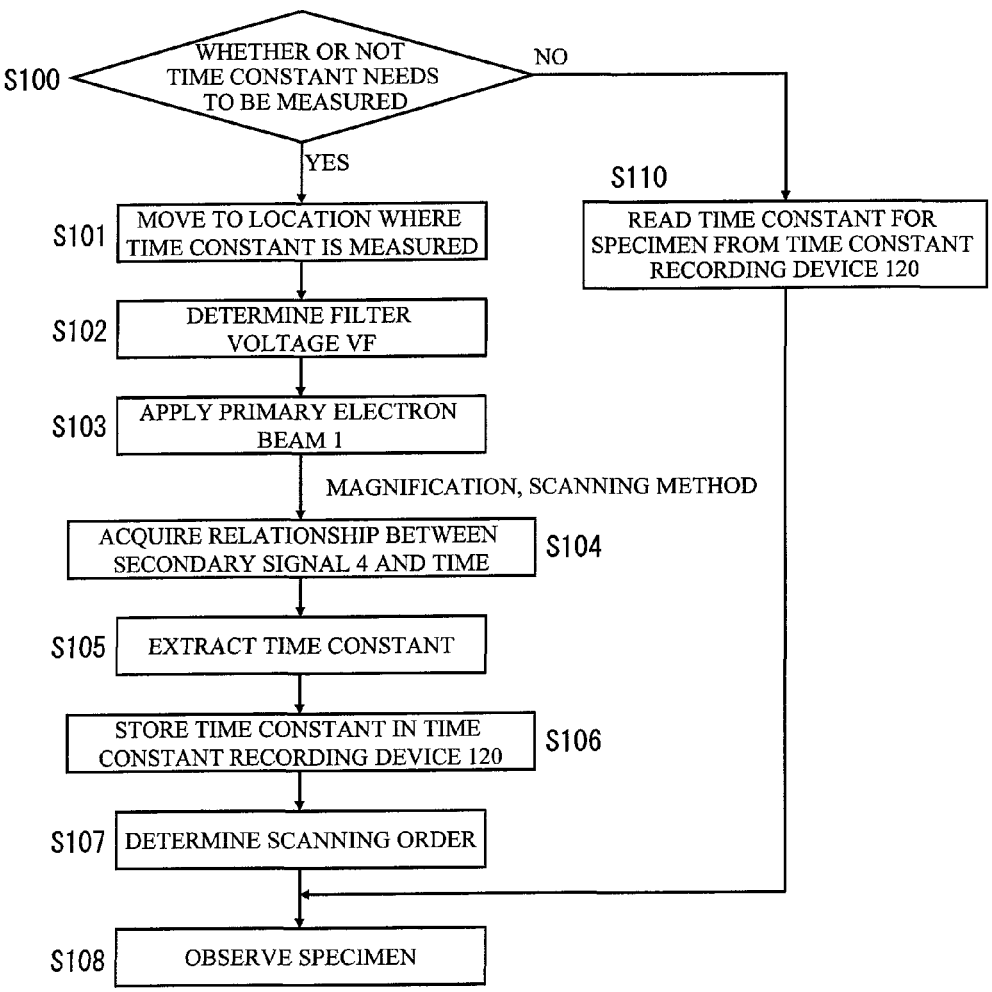
FIG. 3 is a flowchart for explaining the process of determining the scanning order according to the embodiment of the present invention.

FIG. 3 is a flowchart for explaining the process sequence of the SEM according to this embodiment.

In the step S100, it is judged whether or not the time constant has been measured on a sample of the same type or the same wafer in the past and the measured time constant has been stored in the time constant recording device 120. It is then determined whether or not the time constant needs to be measured. When the time constant is to be measured, the electron beam is moved to the location where the time constant is measured in the step S101. The location of the specimen where the time constant is measured is desirably a flat portion, the location to be observed, or the location where a pattern equivalent to the location to be observed is present.

In the next step S102, a blocking potential to be applied to the energy filter 30 is determined, and a filter potential is set accordingly. The filter potential is a potential for capturing high-energy secondary electrons that are not affected by the local distribution of charging on the specimen. Then, in the steps S103 and S104, the specimen 23 is irradiated with the primary electron beam 1 to acquire the relationship between the secondary signal 4 and time (input D1, see FIG. 2).

In the step S105, the input D1 acquired in the step S104 is inputted to the time constant extraction device 110 to extract the time constant $\tau$ for the specimen being observed. The detail of the extraction process will be described later.

In the step S106, the extracted time constant $\tau$ is stored in the time constant recording device 120.

In the step S107, an optimum scanning order is determined based on the extracted time constant and scanning conditions (input D2). The detail of how to determine the scanning order will be described later. The scanning conditions herein refer to the scan interval $\Delta 1$, the number of scans n, and the scan time for one line $\Delta t$.

In the step S108, the scanning order outputted from the scanning order determination device is used to actually observe the specimen. By storing the outputted scanning order in a recording device, SEM images can be acquired in the optimum scanning order without having to measure the time constant and optimize the scanning order at a later time when a specimen is considered to be equivalent in terms of the material, the structure, or the pattern is observed.

When it is judged that no time constant measurement is necessary in the step S100, the process proceeds to the step S110. In the step S110, when the time constant has been measured in the past, the time constant is read from the time constant recording device 120. When no time constant has been measured in the past, the time constant is estimated from the material of the specimen to be observed.

<Process of Acquiring the Relationship of the Energy Filter and the Secondary Signal with Time (Step S104)>

Figure 4:
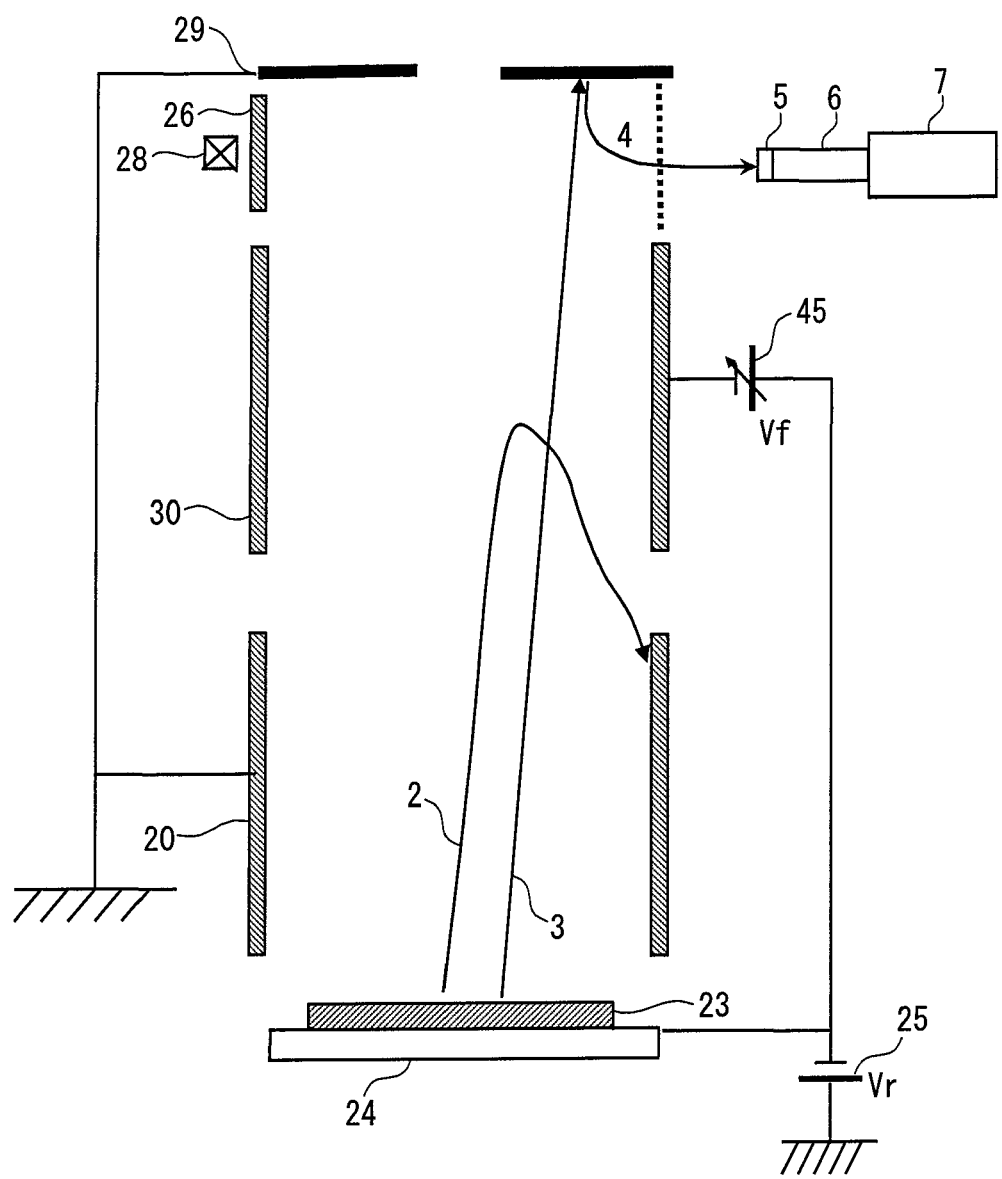
FIG. 4 explains the operation of a blocking potential-type energy filter.

FIG. 4 explains the operation of the energy filter 30. As shown in FIG. 4, when the potential Vr (25: 0 V, for example) and the potential Vf (45: 5 V, for example) are applied to the specimen 23 and the energy filter 30, respectively, the blocking potential Vrf (=Vr−Vf, indicating how much lower the potential is than the potential at the specimen 23) is created. With this setting, among the electrons emitted from the specimen 23, those having higher energy than the blocking potential Vrf can be detected, while those having lower energy cannot be detected.

Figure 5:
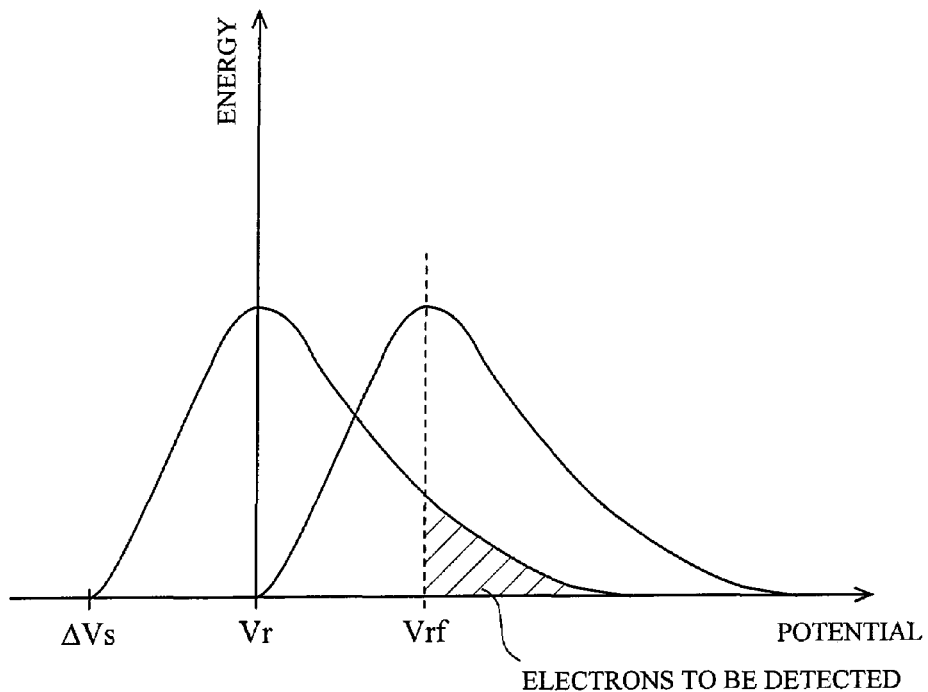
FIG. 5 shows the energy characteristic when electron beam irradiation charges a specimen and the potential thereof rises by $\Delta Vs$.

Now, consider a case where the electron beam irradiation charges the specimen and the potential thereof rises by $\Delta Vs$ (see FIG. 5). At this point, the specimen potential Vs is expressed by Vs=Vr+$\Delta Vs$, so that the blocking potential Vrf (=Vr+$\Delta Vs$−Vf) rises by $\Delta Vs$. Therefore, the number of electrons extracted by the energy filter and then detected decreases, and the brightness of the image thus decreases. Using the principle described above, the charging potential $\Delta Vs$ (the variation from the reference at the location of the specimen under no electron beam irradiation) can be determined from the brightness of the image (the hatched portion in FIG. 5). Alternatively, by adjusting the voltage Vf applied to the energy filter 30 and only looking at the change in yield of high-energy electrons emitted from the specimen 23, highly accurate potential measurement can be carried out without considering the fact that the charging of the specimen changes the trajectory of the emitted electrons.

Specifically, the voltage Vf is applied to the energy filter 30, and the temporal change in brightness of the image formed by the electrons that pass through the energy filter 30 is measured. The temporal change in brightness of the image formed by the electrons that pass through the energy filter is measured by using the image of the observation location or a flat portion of the wafer being observed. In this measurement, the primary electron scanning method may be arbitrarily set according to the purpose (for example, one-point irradiation, line scanning, TV scanning, and random scanning). To improve the S/N ratio, the potential at the filter is set to a fixed value and the above measurement is carried out at a plurality of locations on the wafer being observed.

Furthermore, the change in potential at arbitrary locations can be measured by carrying out the measurement at locations of the wafer where the materials or the pattern shapes are different from one another.

Figure 7:
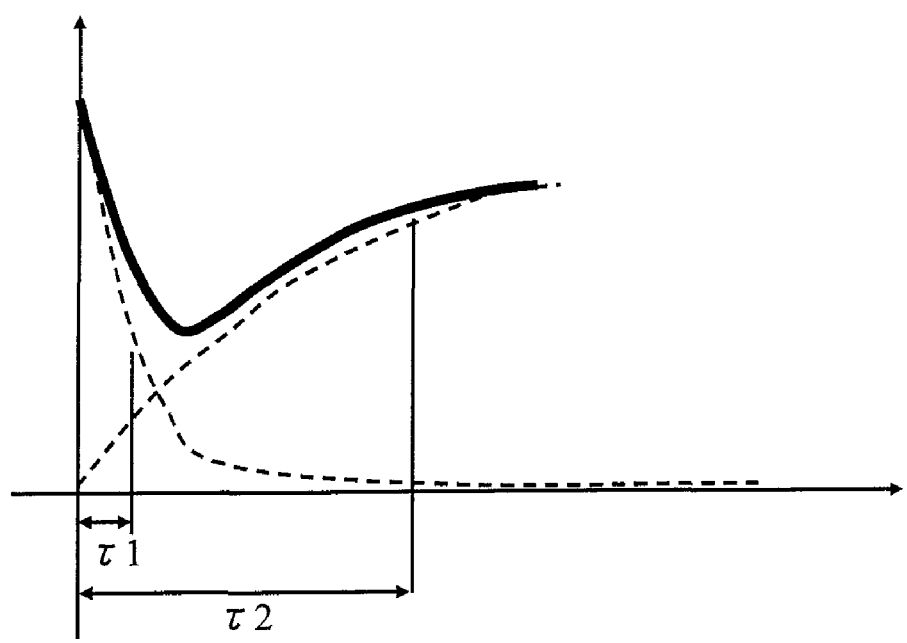
FIG. 7 shows the relationship between the amount of a secondary electron signal and electron beam irradiation time.

Based on these measurement results, a curve S(t) indicative of temporal change in the signal magnitude S is acquired (see FIG. 7).

Figure 6:
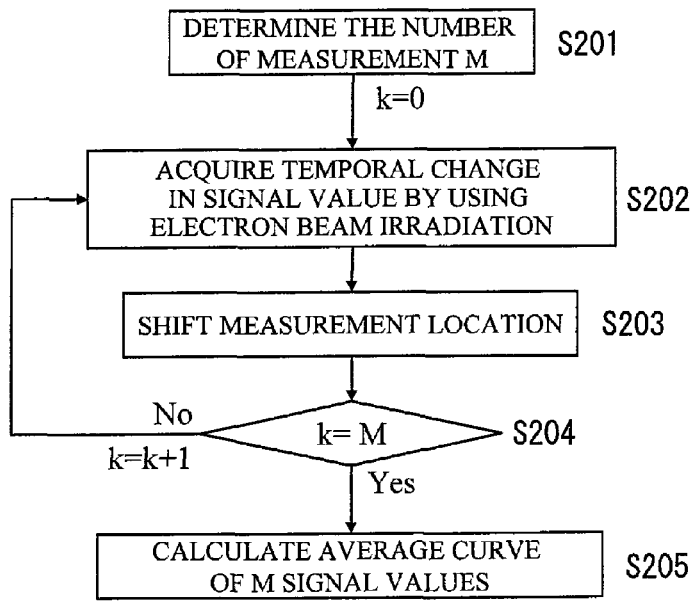
FIG. 6 is a flowchart showing the process for acquiring a temporal change curve indicative of the relationship between a secondary signal and time.

To determine the scanning order, it is necessary to measure the variation in specimen potential on the order of several voltages at a high temporal resolution on the order of a microsecond and extract the time constant. In the potential measurement using an energy filter, there is a trade-off between the temporal resolution and the accuracy of the measured potential. Therefore, at an improved temporal resolution, the S/N of the detected secondary signal 4 decreases, and hence the error in measured potential increases. To address this problem, the secondary signal 4 is measured multiple times by shifting the measurement point multiple times on the wafer. The average of the measured signal values can be used to improve the S/N, and both the accuracy and the temporal resolution of the potential measurement can be kept at satisfactory levels. FIG. 6 shows the sequence of the time constant measurement.

In FIG. 6, the number of measurement M for determining the average of the signal values is determined in the step S201. The number of measurement M is determined by first measuring the signal value once and evaluating the S/N of the measurement result. That is, to obtain the curve indicative of the temporal change in the signal shown in FIG. 7, it is necessary to acquire the relationship between the time and the amount of the secondary electron signal, but only one measurement cannot provide a satisfactory signal. To improve the S/N, the measurement is repeated M times at flat locations.

In the step S202, the temporal change in the secondary signal 4 is acquired by electron beam irradiation. Then, in the step 5203, the measurement location is shifted. In the step S204, the measurement is repeated until the number of measurement reaches M.

Finally, in the step 5205, the average curve is determined from the M measured signal values, which is inputted to the time constant extraction device 110 as the input D1.

FIG. 7 shows the (exemplary) relationship between the signal electrons 4 and the electron beam irradiation time obtained as described above.

<Time Constant Extraction Process (Step S105)>

In the following section, the time constant extraction process carried out in the time constant extraction device 110 will be described in detail.

When the temporal change in signal magnitude is expressed by the following equation: $S=S0\times\exp(-t/\tau)$, where S0 is a coefficient and $\tau$ is the time constant, the time constant $\tau$ is determined by fitting the above equation with S(t) in FIG. 7. That is, when the primary electron beam positively charges the specimen, the signal magnitude changes as shown in FIG. 7. The initial sharp change represents the state in which the electron beam accumulates positive electric charge, so that the brightness decreases. Let $\tau 1$ be the time constant in this state (time constant that characterizes the process in which electron beam irradiation accumulates positive electric charge). The following slow change represents the difference between the dissipation of electrons due to their motion and diffusion as well as the loss of electric charge due to electron-hole recombination and the supply of positive electric charge resulting from the primary electron beam. Let $\tau 2$ be the time constant in this state. The two values, $\tau 1$ and $\tau 2$, are extracted as the time constants of charging. In normal SEM observation conditions, $\tau 1$ is smaller than $\tau 2$.

Now, consider the relationship between the observation time and a SEM image when a specimen whose potential varies at a time constant $\tau$ is observed.

1) When the observation time is sufficiently shorter than the time constant $\tau$, the SEM image will not be distorted because there is no influence of charging. 2) When the observation time is substantially the same as the time constant $\tau$, the influence of the charging changes during the observation, so that the SEM image will be distorted in a non-uniform manner. 3) When the observation time is sufficiently longer than the time constant, the magnification changes, that is, the image will be distorted in a uniform manner because there is continuous influence of charging of the same magnitude during observation.

To minimize the amount of distortion for each line, the time constant closer to the one-line acquisition time is selected and the scanning order may be determined accordingly. On the other hand, to minimize the amount of distortion for each frame, the time constant closer to the one-frame acquisition time is selected and the scanning order may be determined accordingly.

Use of either $\tau 1$ or $\tau 2$ as the time constant is thus judged according to the time required for scanning and characteristic time of the phenomenon under attention. That is, when the scanning order is determined by looking at the time required for scanning (time required for line scanning), the variation in the amount of distortion in one frame is minimized. On the other hand, when the scanning order is determined by looking at the characteristic time of the phenomenon under attention, that is, the time required for observation (time required for acquiring several pixels, several lines, one frame, one image, several images, several tens of images, and more images), the amount of distortion with respect to the time required for observation is minimized.

<Scanning Order Determination Process (Step S107)>

In the following section, the scanning order determination process carried out in the scanning order determination device 130 will be described in detail.

It has been found that the influence of charging accumulated by electron beam irradiation is removed by performing the next scan at a location as far as possible from the location that has been irradiated with the electron beam, or by waiting as long as possible until the next irradiation. However, simply setting longer distance between scans or longer time interval reduces the throughput of image acquisition.

To optimize the scanning method, the relationship among the distance, the time and the electron beam irradiation is quantified as follows:

In the following description, a quantification method will be presented with reference to an example in which the electron beam scan is carried out line by line. Let $\Delta 1$ be the distance from the current scan line to the next scan line, $\Delta t$ be the time required until the next scan starts (scan time), and Q be the amount of charged electric charge. The amount of charged electric charge Q is obtained from the temporal change in signal magnitude described above and expressed by $Q=Q0\times\exp(-\Delta t/\tau)$. Since the force F acting on the electron beam when it scans a position apart from the line that has been scanned last time by 1 is expressed by $F=Q/1$, the amount of deflection of the electron beam $\Delta L$ is expressed by:

$$\Delta L = a \times Q0 \exp(-\Delta t/\tau)/1 \quad (1)$$

where a is a proportionality constant. Now, let n be the number of scan lines in the observation area. Then, the amount of deflection L of the primary electrons across the observation area is expressed by:

$$L = \Sigma \Delta L = \Sigma a \times Q0 \exp(-\Delta t/\tau)/1 \quad (2)$$

Figure 8:
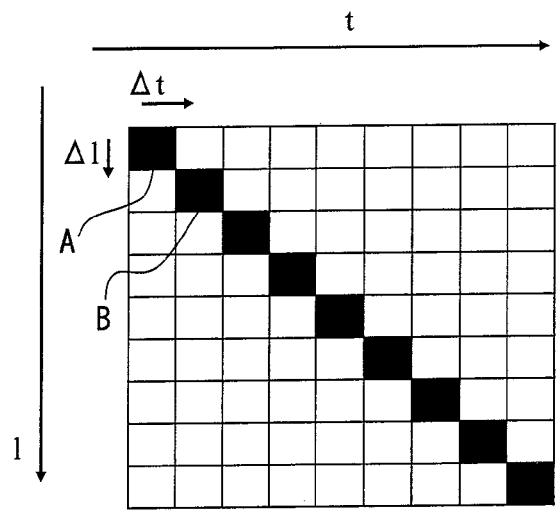
FIG. 8 explains how to determine the scanning order.
Figure 8:
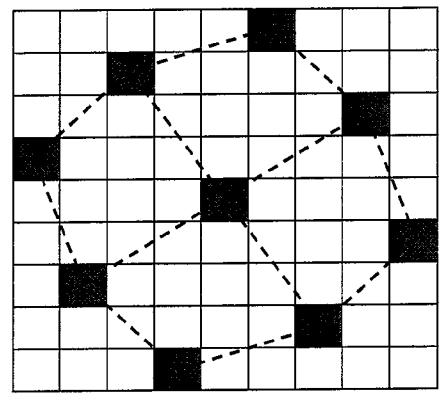
Figure 8:
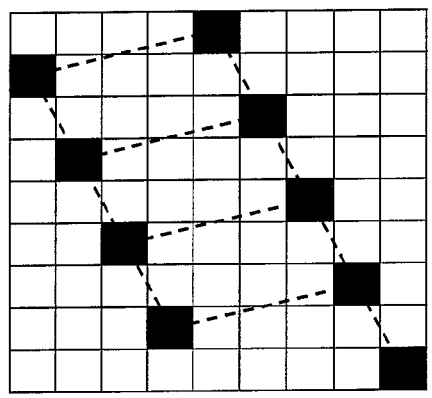
Figure 8:
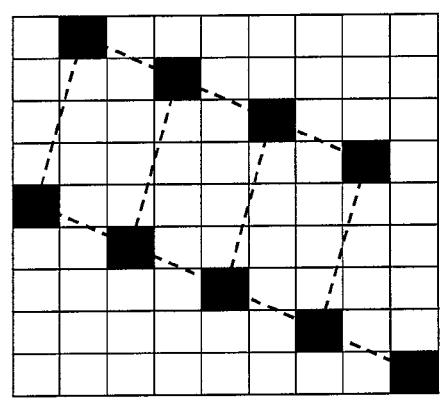

FIG. 8 shows the arrangement of scan points when line scanning is carried out nine times ($\Delta t$: one-line scan time, $\Delta 1$: scan interval) by way of example. FIG. 8(A) shows the arrangement of scan points when scanning is sequentially carried out from the top of the image. Since the top line is scanned in the first scan, the scan point is disposed at A. In the second scan, the next line is scanned $\Delta t$ seconds after the first scan, so that the scan point is disposed at B. In the second scan, the charging created in the first scan affects the primary electrons, which are therefore deflected. The amount of deflection $\Delta L$ at this point is derived from the equation (2) and expressed by $a \times Q0 \times \exp(-\Delta t/\tau)/\Delta 1$. When the scanning is thus sequentially carried out from the top, the influence of the charging created during the previous scan is large because the distance between scan points is small.

To minimize the image distortion due to the charging, the scan points may be arranged in such a way that the total amount of deflection $L=\Sigma\Delta L$ expressed by the equation (2) is minimized. This is equivalent to solving a problem of embedding n scan points in a distance-time space divided into segments apart from one another by $\Delta 1$ and $\Delta t$. In one method, scan points may be disposed in the distance-time space in a uniform manner with no overlap in such a way that the distance between each pair of scan points is maximized. As a result of the above consideration, it is found that the most efficient arrangement (uniform arrangement) is such that the scan points are embedded across the space in a triangular, rectangular, or a hexagonal manner.

When the one-line scan time $\Delta t$ and the scan interval $\Delta 1$ equally affect the amount of deflection of the primary electron beam 1, the arrangement shown in FIG. 8(B) is employed. According to FIG. 8(B), the scanning order is the lines #4→#7→#2→#9→#5→#1→#8→#3→#6, and all the nine lines are scanned in this order.

When the time constant ti for the specimen is larger than that in FIG. 8(B), the shape of the scan points may be laterally extended. On the other hand, when the time constant τ for the specimen is smaller than that in FIG. 8(B), the shape of the scan points may be longitudinally extended. Therefore, the shapes of the scan points are those shown in FIG. 8(C) and FIG. 8(D), respectively. The arrangement methods shown in FIGS. 8(B) to 8(D) are examples in which the scan points are set in a rectangular manner.

As described above, it is found that once the time constant t of the temporal change in the amount of electric charge is determined, the scanning method for minimizing the equation (2) can be uniquely determined.

<Other Embodiments>

In the present invention, the time constant of the temporal change curve indicative of the relationship of the signal magnitude of the electrons caught by the energy filter with the electron beam irradiation time may be recorded in the time constant recording device 120 in advance for each of a plurality of specimens, and the recorded time constant may be used to determine an optimum scanning order for the specimen. That is, the user uses input means (not shown), such as a keyboard and a mouse, to specify a specimen to be observed. Then, the time constant corresponding to the specified specimen is read from the time constant recording device 120, and the scanning order in which the electron beam scans the specimen to be observed is determined based on the time constant. The method for determining the scanning order is the same as that described above.

Alternatively, an optimum scanning order in which the electron beam scans the specimen may be stored in a memory (not shown) in advance for each specimen to be observed, and the stored scanning order may be used to observe the specimen. That is, the user uses input means (not shown), such as a keyboard and a mouse, to specify a specimen to be observed. Then, the scanning order corresponding to the specified specimen is read from the memory, and the primary electron beam scans the specimen based on the scanning order. The optimum scanning order stored in the memory has been determined for each specimen by using the method described above.

<Summary>

In this embodiment, among the electrons emitted from the specimen, those having at least a predetermined energy level are caught by the energy filter. Then, the time constant of the temporal change curve indicative of the relationship between the signal magnitude of the caught electrons and the electron beam irradiation time is extracted, and the scanning order in which the electron beam scans the specimen is determined based on the time constant. Among the electrons emitted from the charged specimen, the energy filter is thus used to eliminate low-energy electrons and catch high-energy electrons that are less affected by the charging, so that the charging potential can be estimated in a more accurate manner. The time constant to be extracted can therefore be measured at a temporal resolution on the order of a microsecond, so that the extracted time constant can be used to determine an optimum scanning order.

The scanning order is determined based on the extracted time constant as well as the scanning conditions defined by the one-line scan time and the scan interval in such a way that scan points are arranged in the time-distance space and the distance between each pair of scan points is maximized. In this way, the influence of charging created during the previous scan can be minimized. By determining the scanning order in such a way that the scan points are arranged in a triangular, rectangular, or hexagonal manner, the distance between each pair of scan points can be large, so that the most efficient arrangement is achieved without large influence of the charging created by each scan on the other scans.

Furthermore, the aspect ratio of the scan points arranged in the time-distance space may be changed according to the result of comparison of the time constant of potential variation resulting from the electron beam irradiation with a reference time constant. That is, when the time constant is greater than the reference time constant T in FIG. 8(B), the shape of the figure formed of the scan points (a rectangle, for example) is laterally extended (FIG. 8(C)), while when the time constant is smaller than the reference time constant T, the shape is longitudinally extended (FIG. 8(D)). By thus determining the scanning order, an optimum scanning order can be uniquely determined.

To extract the time constant, the filter potential at the energy filter is set to a fixed value, and the temporal change in brightness when the specimen is irradiated with the primary electron beam is used to extract the time constant of the potential variation. Since highly accurate potential measurement can be carried out by only looking at the change in yield of the thus detected electrons, more accurate temporal change curve of the signal magnitude can be acquired and hence an accurate time constant can be extracted. To further improve the S/N, the measurement is repeated by shifting the irradiation position of the primary electron beam, and the average of the temporal changes in brightness obtained at a plurality of positions may be used to provide the temporal change curve.

What is claimed is:

1. A scanning electron microscope in which a specimen is irradiated with a primary electron beam to acquire an image of the specimen, the scanning electron microscope comprising:
    a deflector, which scans the specimen with the primary electron beam:
    an energy filter, which selectively permits electrons having more than a predetermined energy level among the electrons emitted from the specimen to pass;
    a detector, which outputs a detection signal based on the electrons that have passed through the energy filter; and
    a scanning order determination device, which determines a scanning order of a scanning line of the deflector, the scanning order being determined in response to a temporal change of an intensity of the detection signal outputted from the detector.

2. The scanning electron microscope according to claim 1, wherein the scanning order determination device determines the scanning order by selecting one of plural scanning patterns in response to the temporal change of the intensity of the detection signal.

3. The scanning electron microscope according to claim 1, further comprising a time constant extraction device that measures the temporal change of the intensity of the detection signal.

4. The scanning electron microscope according to claim 3, wherein the time constant extraction device measures the temporal change of the intensity of the detection signal based on a change in yield of the electrons detected by the detector where a filter voltage of the energy filter is set to a fixed value.

5. The scanning electron microscope according to claim 1, wherein the deflector scans the specimen with the primary electron beam at a scanning interval that varies in response to the temporal change of the intensity of the detection signal.

* * * * *